US012575731B2

(12) United States Patent
Trittibach et al.

(10) Patent No.: US 12,575,731 B2
(45) **Date of Patent: \*Mar. 17, 2026**

(54) OPHTHALMOLOGIC MICROSCOPE WITH MICRO-MIRROR BALANCING

(71) Applicant: Haag-Streit AG, Köniz (CH)

(72) Inventors: Caspar Trittibach, Bern (CH); Frank Zumkehr, Zollikofen (CH)

(73) Assignee: Haag-Streit AG, Köniz (CH)

( * ) Notice: Subject to any disclaimer, the term of this patent is extended or adjusted under 35 U.S.C. 154(b) by 919 days.

This patent is subject to a terminal disclaimer.

(21) Appl. No.: 17/792,029

(22) PCT Filed: Jan. 13, 2020

(86) PCT No.: PCT/EP2020/050727

§ 371 (c)(1),
(2) Date: Jul. 11, 2022

(87) PCT Pub. No.: WO2021/144000

PCT Pub. Date: Jul. 22, 2021

(65) Prior Publication Data

US 2023/0049486 A1 Feb. 16, 2023

(51) Int. Cl.
*A61B 3/12* (2006.01)
*A61B 3/00* (2006.01)
(Continued)

(52) U.S. Cl.
CPC .............. *A61B 3/13* (2013.01); *A61B 3/0008* (2013.01); *A61B 3/14* (2013.01); *A61B 2560/0223* (2013.01)

(58) Field of Classification Search
CPC .......... G02F 1/0123; G02F 1/31; G02F 1/093; G02F 1/293; G02F 1/3538; A61H 5/00;
(Continued)

(56) References Cited

U.S. PATENT DOCUMENTS 5,801,758 A * 9/1998 Heirich ................. H04N 7/144
348/14.08
5,943,118 A 8/1999 Koschmeider et al.
(Continued)

FOREIGN PATENT DOCUMENTS

CN 101733549 6/2010
EP 0 911 667 4/2003
(Continued)

OTHER PUBLICATIONS

"Texas Instruments data sheet for DLP4710 0.47 1080p DMD", (DLPS056B—Nov. 2014—Revised Jul. 2016), URL Link: https://www.ti.com/lit/ds/dlps056b/dlps056b.pdf.
(Continued)

*Primary Examiner* — Dawayne Pinkney
(74) *Attorney, Agent, or Firm* — GREENBLUM & BERNSTEIN, P.L.C.

(57) ABSTRACT

The ophthalmologic microscope has an illumination device for projecting light onto an eye to be observed and a microscope device with a camera to view the eye. The illumination device generates pulsed light. The light is pulsed at least at twice the frame rate of the camera to reduce flicker. The illumination device uses an array of micro-mirrors as spatial light modulator, and the mirrors are controlled for a balanced deflection over the frame cycles, which allows to increase the service life of the microscope.

24 Claims, 2 Drawing Sheets

(51) Int. Cl.

| | | |
|---|---|---|
| *A61B 3/10* | (2006.01) | |
| *A61B 3/13* | (2006.01) | |
| *A61B 3/14* | (2006.01) | |
| *G02B 27/02* | (2006.01) | |

(58) Field of Classification Search

CPC .. G02B 26/001; G02B 27/283; G02B 6/2766; H04B 10/505; H04B 2203/50; B82Y 20/00; A61B 3/103; A61B 3/14; A61B 3/1015; A61B 3/1205; A61B 3/113

USPC ....... 351/221, 200, 205–206, 203, 215, 246, 351/210, 211; 359/238, 239, 278–279, 359/245, 299–304

See application file for complete search history.

(56) References Cited

U.S. PATENT DOCUMENTS

| | | | | |
|---|---|---|---|---|
| 6,361,167 | B1 | 3/2002 | Su et al. | |
| 6,399,935 | B1 | 6/2002 | Jovin et al. | |
| 7,905,598 | B2 | 3/2011 | Kishida et al. | |
| 7,922,327 | B2 | 4/2011 | Su et al. | |
| 10,634,907 | B1 * | 4/2020 | Geng | G02B 27/283 |
| 2004/0041824 | A1 * | 3/2004 | Willis | G09G 3/2029 |
| | | | | 345/691 |
| 2005/0195360 | A1 | 9/2005 | Akita et al. | |
| 2007/0165245 | A1 | 7/2007 | Gomercic et al. | |

| | | | | |
|---|---|---|---|---|
| 2009/0135313 | A1 * | 5/2009 | Endo | G03B 21/005 |
| | | | | 348/E5.142 |
| 2014/0043439 | A1 | 2/2014 | Sichler et al. | |
| 2014/0232763 | A1 | 8/2014 | Hada et al. | |
| 2016/0062121 | A1 | 3/2016 | Border et al. | |
| 2016/0202463 | A1 | 7/2016 | Foelling | |
| 2019/0391382 | A1 * | 12/2019 | Chung | G02B 21/367 |
| 2020/0033575 | A1 * | 1/2020 | Mueller | G02B 21/02 |

FOREIGN PATENT DOCUMENTS

| | | | | |
|---|---|---|---|---|
| JP | 2005-237901 | 9/2005 | | |
| JP | 2011-235120 | 11/2011 | | |
| JP | 2012-212095 | 11/2012 | | |
| WO | WO-2006080023 A1 * | 8/2006 | ........ | G01N 21/8806 |
| WO | 2009/145048 | 12/2009 | | |
| WO | 2011/119602 | 9/2011 | | |

OTHER PUBLICATIONS

Int'l Search Report (Form PCT/ISA/210) conducted in Int'l Appln. No. PCT/EP2020/050727 (Oct. 9, 2020).

Int'l Written Opinion (Form PCT/ISA/237) conducted in Int'l Appln. No. PCT/EP2020/050728 (Oct. 9, 2020).

Translation of Japan Office Action conducted in counterpart Japan Appln. No. 2022-542734 (Oct. 24, 2023).

China Office Action conducted in counterpart China Appln. No. 202080091355 (Mar. 25, 2025).

* cited by examiner

OPHTHALMOLOGIC MICROSCOPE WITH MICRO-MIRROR BALANCING

TECHNICAL FIELD

The invention relates to ophthalmologic microscopes, in particular slit lamp microscopes, having an illumination device adapted to generate illumination pulses on the eye and a microscope device with a camera for recording images of the eye. In particular, it relates to a microscope where the illumination device comprises an electronically controlled spatial light modulator comprising a two-dimensional array of micro-mirrors.

The invention also relates to methods for operating such a device.

BACKGROUND ART

U.S. Pat. No. 5,943,118 describes an ophthalmologic microscope having an illumination device generating illumination pulses as well as a microscope having a camera. The device comprises an electronically controlled spatial light modulator comprises a spatial light modulator having an array of micro-mirrors, where each micro-mirror can be controlled electronically and be brought into an on- or off-position, which allows to generate arbitrary illumination patterns on the eye to be observed.

DISCLOSURE OF THE INVENTION

The problem to be solved by the present invention is to improve the service life of such a device.

This problem is solved by the device and method according to the independent claims.

Accordingly, the invention relates to ophthalmologic microscopes comprising at least the following elements:

i) An illumination device generating illumination pulses: The illumination device is adapted and structured to generate individual light pulses for illuminating the eye to be examined. It comprises at least the following elements:

a) At least one light source: This is the part of the illumination device that generates the light.

b) An electronically controlled spatial light modulator: This part is structured to spatially modulate the light. The spatial light modulator comprises a two-dimensional array of micro-mirrors, with each micro-mirror individually deflectable into a first and a second position. In this context, a micro-mirror is advantageously a mirror having an area of less than 1 mm$^2$, in particular less than 100 μm$^2$.

c) Illumination imaging optics: This part is structured to project the light onto the eye. Advantageously, it projects an image of the spatial light modulator onto the eye, thereby generating a defined illumination pattern on the eye.

ii) A microscope device: The microscope device is adapted to record an image of the eye. It comprises at least the following elements:

a) Microscope optics: The microscope optics generates an image of the eye.

b) At least one electronic camera: The camera is adapted to record the projected image from the microscope optics. The images are recorded in repetitive frame cycles. In each frame cycle, one frame of the image is recorded by the camera.

iii) A control unit: The control unit controls the operation of the elements of the device.

According to a first aspect of the invention, the camera has a frame signal output carrying a signal indicative of the times when the camera records a frame. In particular, it may generate a single pulse synchronized to each frame it takes, i.e. synchronized to the integration phase of that frame.

The control unit is structured to bring, for a group of N≤100 consecutive frame cycles of the camera, each micro-mirror of the spatial light modulator into the first position during a time t1 and into the second position during a time t2. In other words, t1 corresponds to the time a given micro-mirror is in its first position during the group of N consecutive frame cycles, and t2 corresponds to the time the given micro-mirror is in its second position during the same group of N consecutive frame cycles. According to the invention, t1 and t2 are balanced in the sense that $0.1 < t1/t2 < 10$.

Note, t1 and t2 are typically different for at least some of the micro-mirrors, i.e. t1 and t2 are, in a most general case, dependent on the location i, j of the mirror in the modulator.

The invention takes into account that the service life of such a spatial light modulator is increased by balancing the positions of the micro-mirrors. For light modulators used in image or movie projection, such balancing is naturally achieved by the images or movie frames and their RGB-channels varying constantly. In an ophthalmologic microscope, though, the illumination patterns are the same or similar for a large number of examinations, which leads an unbalance in the mirrors' positions. Such an unbalance could be compensated for by simply moving the mirrors into their less used positions when the microscope is not in used for examinations. The present invention, though, is based on the understanding that balancing can also take place while the device is used, i.e. while consecutive frames are recorded. This obviates the need to carry out balancing when the device is not in use.

The balancing is advantageously carried out over each individual frame cycle, i.e. N=1. This simplifies the operation of the device because it obviates the need to "plan" the mirror positions over two or more frame cycles.

The closer the ratio of t1 and t2 is to 1, the better the balancing becomes. Hence, advantageously, $0.2 < t1/t2 < 5$, in particular $0.33 < t1/t2 < 3$.

The light source is advantageously pulsed, i.e. the control unit is structured to pulse the light source. Advantageously, this is done in a manner synchronized with the frame cycles of the camera.

If the microscope uses a pulsed illumination, the control unit may be adapted to:

bringing the pixels into a given configuration during a dark phase prior to a given light pulse, and starting the light pulse only when the pixels are in the desired configuration.

In this case, the dark phase is before a light pulse is exploited for setting up the light modulator. This setting up may take some time, e.g. because the pixels are slow or because it takes time to feed the pattern information sequentially into the light modulator, and it is therefore best done before the light pulse.

The device may further comprise several light sources and at least one light detector adapted to measure the light intensity at a location between the light sources and the spatial light modulator, i.e. the brightness of the light source independently of the state of the light modulator. In that case, the method or control unit may be adapted to perform at least the following two steps:

Bringing the light modulator into a non-transmitting mode: In this mode, no light is projected onto the eye even if the light source is switched on.

While the light modulator is in this non-transmitting mode, pulsing one light source for measuring the brightness of this light source.

This allows to intermittently—in particular while recording of a series of image frames—control the current brightness of the light source. This information can then be used e.g. for adjusting the current through the light source during light pulses while recording the frames on the on-time of the pixels of the light modulator while recording the frames in order to achieve a defined illumination.

BRIEF DESCRIPTION OF THE DRAWINGS

The invention will be better understood and objects other than those set forth above will become apparent when consideration is given to the following detailed description thereof. Such description makes reference to the annexed drawings, wherein.

MODES FOR CARRYING OUT THE INVENTION

Overview

Figure 1:
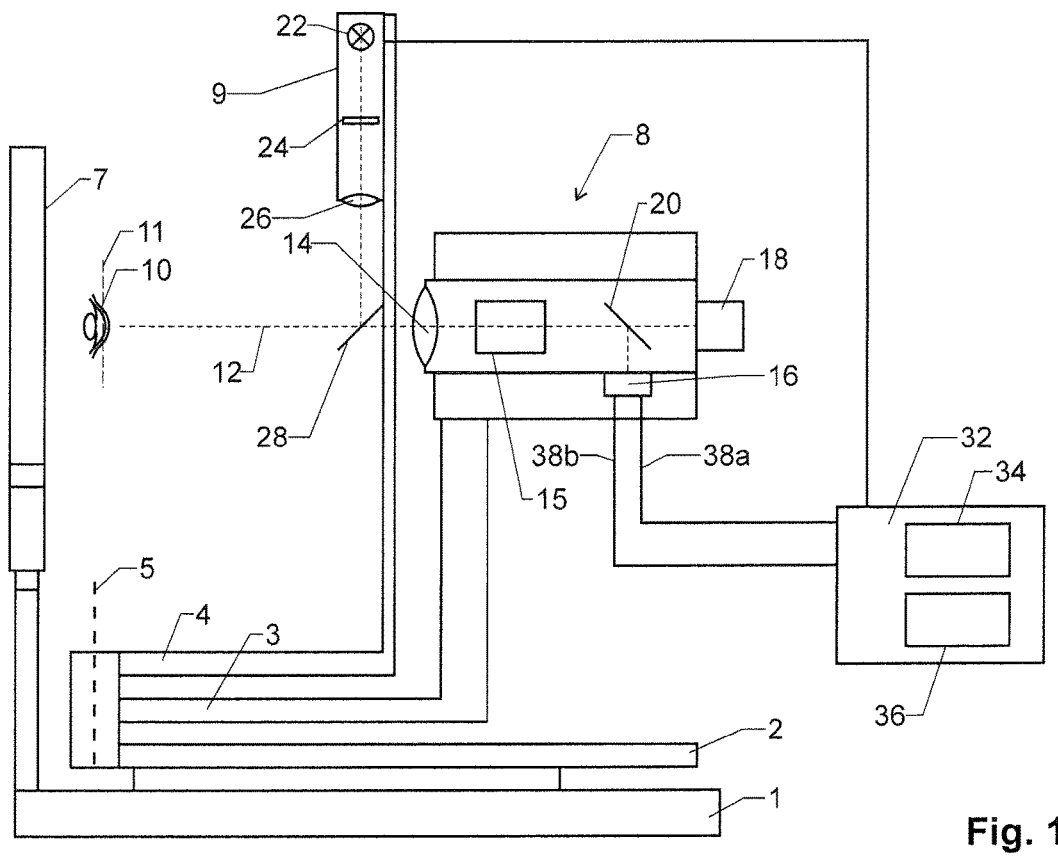
FIG. 1 shows an embodiment of an ophthalmologic microscope.

FIG. 1 shows an embodiment of an ophthalmologic microscope, in particular a slit lamp microscope.

The microscope has a base 1 resting e.g. on a desk, a translationally displaceable stage 2 mounted to base 1, a first arm 3, and a second arm 4.

Stage 2 can be linearly displaced along horizontal directions x and z in respect to base 1.

The arms 3 and 4 are mounted to stage 2 and pivotal about a common vertical pivot axis 5, i.e. an axis parallel to vertical direction y.

The device may further include a headrest 7 mounted to base 1 for receiving the patient's head.

Arm 3 carries a microscope device 8, and arm 4 carries an illumination device 9, such as a slit lamp.

Microscope device 8 has an optical axis 12. It comprises microscope optics 14, 15, such as an objective 14 and zoom optics 15, which project an image of eye 10 onto a camera 16 and, optionally, an eyepiece 18. A beam splitter 20 may be provided to spilt light between these components.

Illumination device 9 is adapted to project a structured light beam onto the eye 10 to be examined. It comprises a light source 22, a spatial light modulator 24, and illumination imaging optics 26.

Light source 22 can e.g. comprise several units emitting different wavelengths, e.g. in the red, green, blue, and infrared range of the optical spectrum. These units can be controlled separately in order to change the color of light source 22.

Advantageously, the light source 22 comprises at least one LED and/or semiconductor laser. This type of light sources are advantageous because LEDs and semiconductor lasers can be pulsed rapidly and precisely.

Illumination imaging optics 26 projects the light from modulator 24 onto e.g. the anterior surface of eye 10, e.g. via a mirror 28 mounted to arm 4. The anterior surface of eye 10 is assumed to be located at a target plane 11, which is the optically conjugate plane of spatial light modulator 24 in respect to illumination imaging optics 26.

Illumination device 9 can be arranged above or below mirror 28.

A control unit 32 controls the components of the microscope. In particular, it may e.g. comprise a microprocessor 34 and a memory 36. Microprocessor 34 is programmed to carry out the steps of the method as described below, and memory 36 contains the data and/or instructions to do so.

Camera 16 has is adapted to record a series of individual frames of the image projected onto it.

It has a frame signal output 38a carrying a signal indicative of the time when a frame is recorded. It also has a data output 38b for transferring the recorded image. Both outputs 38a, 38b may be connected to control unit 32.

Camera 16 may e.g. by a CCD camera or any other semiconductor-based camera, such as a camera of the IMX series by Sony.

In semiconductor cameras, the process of recording a frame in-volves the integration of the optical signal over a certain period. At the end of the integration period, the image can be read out.

The signal at frame signal output 38a is in synch with this integration phase and, depending on camera type, it may e.g. be issued at the beginning or the end of the integration phase.

Illumination Device

Figures 2, 3:
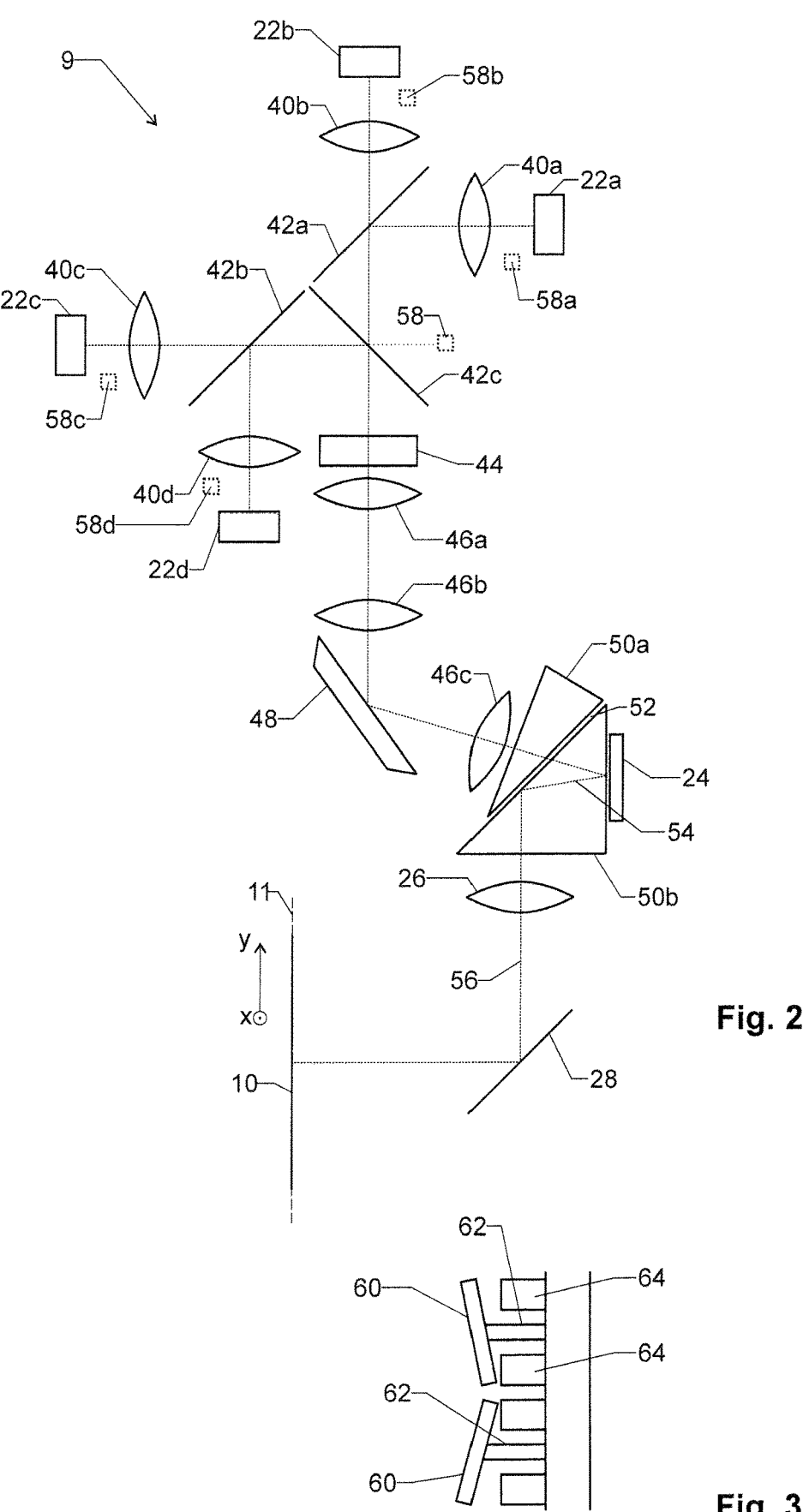
FIG. 2 shows an embodiment of the components of the illumination device.
FIG. 3 is a schematic representation of micro-mirror-based spatial light modulator.

FIG. 2 shows a more detailed embodiment of illumination device 9. It is designed to project an illumination field of defined, sharp contours onto target, such as the eye 10. The illumination field may e.g. be round, rectangular, or slit-shaped. Even though the illumination device is called a "slit-lamp" herein, the illumination field does not need to be slit-shaped at all. It can take any shape.

In the present embodiment, illumination device 9 comprises four light sources 22a-22d of different spectral emission characteristics. For example, they may include an infrared light source, a red light source, a green light source, and a blue light source. Advantageously, the light sources are LEDs. In particular, each light source may be a single LED.

The light from each light source is substantially collimated by means of collimation optics 40a-40d.

Three dichroic mirrors 42a, 42b, 42c are used to combine the light from the light sources 22a-22d to become coaxial.

The combined light is passed through homogenization optics 44, such as a fly-eye lens array, e.g. as described in U.S. Pat. No. 6,507,434.

Two cylindrical lenses 46a, 46b, a further lens 46c, and the homogenization optics 44 together also widen the light beam along one direction, e.g. giving it an elongate cross-section, e.g. having a width-to-height ratio of 16:9, for better matching the typically available form factor of spatial light modulators.

A mirror 48 deflects the light into an assembly of two prisms 50a, 50b with a gap 52 between them.

The light beam passes prism 50a, gap 52, and prism 50b and arrives at spatial light modulator 24.

In the shown embodiment, spatial light modulator 24 is a DMD ("digital micro-mirror device") with a two-dimensional array of individually deflectable micro-mirrors. Control unit 32 is adapted to control the alignment of each micro-mirror, e.g. between a first and a second position.

FIG. 3 shows, schematically, a sectional view of two micro-mirrors 60 of such a DMD. Each mirror 60 is held by an elastic support 62 and deflectable by means of electrodes 64. Devices of this type are known to the skilled person.

For the micro-mirrors 60 being in the first position, the light is reflected back into prism 50*b* along a direction denoted by 54 in FIG. 2. Light traveling along this direction 54 is subject to total internal reflection at the interface of second prism 50*b* to gap 52 and reflected into a direction denoted by 56 in FIG. 2.

For the micro-mirrors 60 being in the second position, the light is still reflected back into prism 50*b*, but along a different direction (not shown in FIG. 2), along which it does not fulfil the conditions for total internal reflection at the interface to gap 52. The small fraction still reflected at this interface will travel in a direction different from direction 56 and not be further processed by illumination imaging optics 26 described in the following.

Hence, control unit 32 is able to individually set each pixel (each micro-mirror 60) of spatial light modulator 24 into an on-state and an off-state, thereby defining the contour and shape of the light field at target 10 (which is assumed to be located in the target plane 11 of the illumination device).

The light from the pixels of spatial light modulator 24 enters illumination imaging optics 26, which may include one or more lenses. From there, it may pass mirror 28 to arrive at target 10.

The illumination imaging optics images spatial light modulator 24 onto target 10, i.e. target 10 is at the target plane 11, which is the conjugate plane, in respect to illumination imaging optics 26, of the plane 62 of spatial light modulator 24.

Operation

Figure 4:
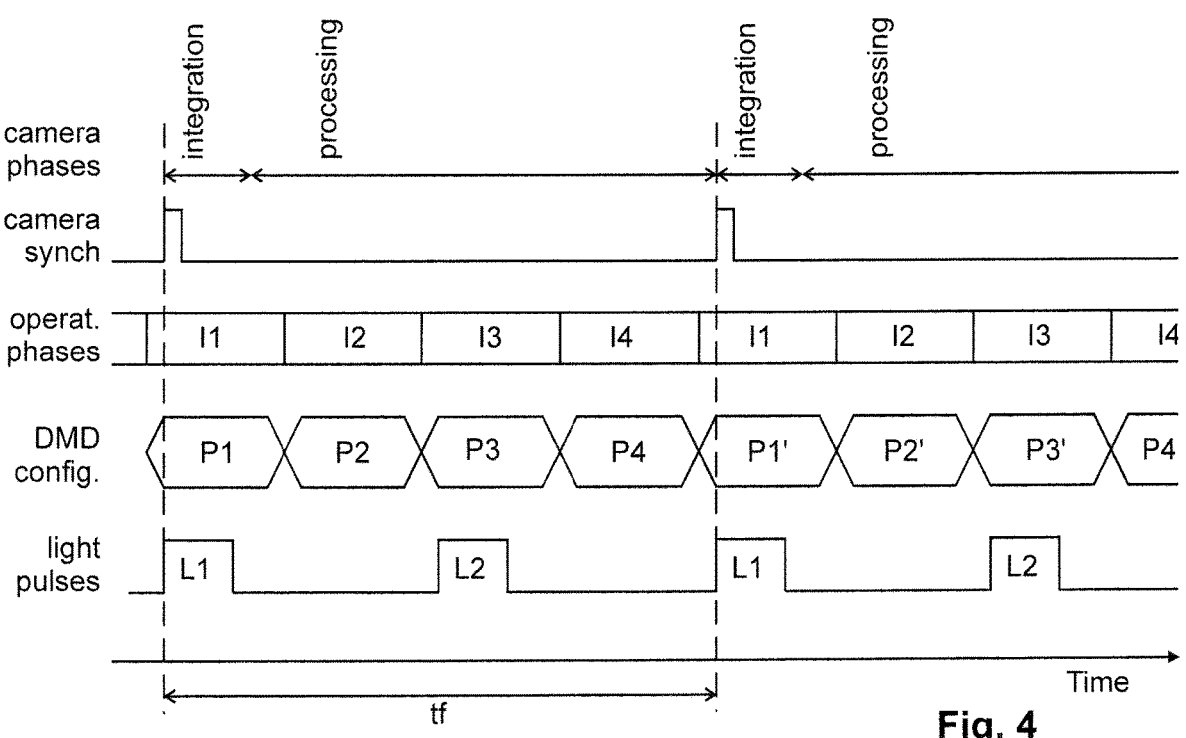
FIG. 4 shows an embodiment of a timing diagram for various components of the device.

The process of recording a series of frames by means of camera 16 is illustrated in FIG. 4.

As can be seen in the first line of FIG. 4, the camera runs through integration and processing phases, which may also at least partially overlap.

In each integration phase, the pixels of the camera integrate the light impinging on them. Then, the respective signal is locked, converted to a digital value, and read out by control unit 32 during a processing phase. This process repeats itself in repetitive frame cycles.

Advantageously, camera 16 is operated in free-running mode, i.e. it repetitively records frames without waiting for external trigger signals. This allows to operate camera 16 at a high frame rate.

Each integration phase is marked by a camera synch signal, as shown in the second line of FIG. 4. If camera 16 is operating in free-running mode, this is the signal on frame signal output 38*a*.

Depending on the specific hardware used, the signal "camera synch" may e.g. coincide with the beginning or the end of the integration phase.

Control unit 32 operates spatial light modulator 24 and light source 22 in synchronicity with the "camera synch" signal as shown in the third to fifth lines of FIG. 4.

In the shown embodiment, control unit 32 operates illumination device 9, during one frame cycle, in four operating phases I1, I2, I3, and I4. They are re-peated in each frame cycle. The integration phase of the camera falls into operating phase I1, while the operating phases I2-I4 are outside the integration phase.

In operating phase I1, spatial light modulator 24 is configured for the appropriate configuration (pattern) P1 of pixels. Advantageously, this configuration is completely set up before the integration phase starts (see fourth line of FIG. 4).

Only then, light source 22 is switched on (see fifth line of FIG. 4) to start a first light pulse L1.

In the shown example, configuration P1 is maintained over the whole integration phase. Also, the light source 22 remains switched on over the whole integration phase (light pulse L1).

When the integration phase has ended, light source 22 is switched off.

The integration phase may be shorter than first operating phase I1.

In operating phase I2, spatial light modulator 24 is brought into a second configuration (pattern) P2 while light source 22 remains switched off.

In operating phase I3, spatial light modulator 24 is brought into a third configuration (pattern) P3, and light source 22 is switched on again in order to generate a light pulse L2, which is switched off again before or at the end of operating phase I3.

In operating phase I4, spatial light modulator 24 is set to a fourth configuration (pattern) P4 and light source 22 remains switched off.

Then, the process repeats with phases I1-I4 and with possible different configurations P1', P2', P3', P4'.

In one embodiment, the configurations are as follows:

Configuration P1 corresponds to the illumination pattern that is desired during recording of the respective frame. It may remain unchanged over the whole integration phase. Alternatively, however, it may be changed during the integration phase, e.g. by switching individual pixels from their on-state to their off-state in order to individually decrease the illumination brightness of said pixels.

Configuration P3 advantageously corresponds to configuration P1, i.e. it has the same pixels switched on and off as configuration P1. This generates two identical illumination patterns on the eye at twice the framerate, thereby reducing flicker as described above.

Configurations P2 and P4 are advantageously the "opposite" of configurations P1 and P3, i.e. when a pixel is on in configuration P1 or P3, the same pixel is off in configuration P2 and P4, and vice versa. This is based on the understanding that the time to failure of DMD spatial light modulators can be increased by regularly bringing each mirror into both its positions for similar periods of time. The present embodiment uses the dark phases between the light pulses L1, L2 to do that.

Advantageously, the operating phases I1-I4 have equal or similar lengths in order to compensate the strain in the supports 62 of the mirrors 60 of spatial light modulator 24. Advantageously, the longest one of the operating phases I1-I4 is no more than 10 times, in particular no more than five times, in particular no more than 3 times, as long as the shortest one of the operating phases I1-I4.

The scheme of FIG. 4 achieves two goals:

1. It balances the mirror deflection in spatial light modulator 24, thereby reducing aging of the modulator.

2. It allows to generate light pulses at the double framerate of camera 16, thereby reducing flicker.

In order to achieve goal 1, in more general terms, control unit 32 may be configured to bring, over one frame cycle (i.e. over one cycle of the integration and processing phase) of camera 16, i.e. for each frame, each micro-mirror 60 of spatial light modulator 24 into its first position during a time t1 and into its second, opposite position during a time t2, where t1 and t2 are comparable, i.e. where $$0.1 < t1/t2 < 10, \tag{1}$$

in particular wherein $$0.2 < t1/t2 < 5, \tag{2}$$

and in particular wherein $$0.33 < t1/t2 < 3. \tag{3}$$

In order to achieve goal 2, in more general terms, control unit 32 may be configured to generate, over one frame cycle of camera 16, i.e. for each frame, at least two separate light pulses, wherein one of the light pulses falls into the integration phase of camera 16 while the other light pulse(s) falls outside the integration phase.

Advantageously, the light pulses L1, L2 have equal durations (in particular within 10%) and, for all light pulses, spatial light modulator 24 has the same configuration (pattern), and the light pulses are separated by dark phases of equal length (i.e. the dark phases have equal length, in particular within 10%). This further reduces flicker.

Advantageously, the repetition rate of the light pulses is at least 70 Hz.

If goal 1 is not required (e.g. because a spatial light modulator not sensitive to unbalanced pixel settings is used, e.g. an LCD modulator), the configuration of spatial light modulator 24 may be any pattern during operating phases I2 and I4.

If goal 2 is not required (e.g. because the frame rate of camera 16 is inherently high enough to avoid flicker effects), operating phases I3 and I4 may be omitted.

If goals 1 and 2 are both to be achieved, control unit 32 is advantageously adapted to bring spatial light modulator 24, between the light pulses L1, L2, into configurations P2 and P4 opposite to the configurations P1 and P3 during the light pulses. In this context, "opposite" first and second configurations means that that if, in the first configuration, a given pixel is in its first state during a time ta and its second state during a time tb, in the second configuration it will be (within an ac-curacy of 10% or better) in its first state during time tb and its second state during time ta.

If the process shown in FIG. 4 is to be synchronized to frame signal output 38*a*, the operating phases I1-I4 should be synchronized to the integration phases of camera 16, such that each integration phase falls into a defined position of first operating phase I1.

To do so, control unit 32 is advantageously adapted to predict the time when camera 16 will record a next frame because, for example, it may need to configure spatial light modulator 24 before the integration phase of camera 16 starts, i.e.—in the embodiment of FIG. 4—before the camera synch pulse arrives.

For this purpose, control unit 32 may e.g. use an estimate of the time tf between two consecutive frames.

This estimate for time tf can e.g. be a value stored in control unit 32 by the manufacturer. Alternatively, control unit 32 can measure it during operation, i.e. it can determine it from the times when camera 16 recorded previous frames.

Then, depending on the time when camera 16 recorded the last frame, i.e. depending on the time of the last camera synch pulse, the time of the next camera synch pulse, i.e. of the next integration phase, can be predicted.

This allows control unit 32 to prepare at least part of illumination device 9, such as spatial light modulator 34 and/or light source 22, before the predicted time of the next integration phase.

Position Balancing of the Micro-Mirrors

As mentioned above in reference to relation (1), (2), or (3), the positions of the micro-mirrors 60 are advantageously balanced, at least to some degree, in order to reduce mechanical strain.

This balancing takes place over no more than N consecutive frame cycles of the camera, i.e. it may not be fulfilled for each single frame cycle, but over the total times t1 and t2 over of a larger number N of frame cycles, with N≤100, may fulfill the relations (1), (2), or (3).

Advantageously, though, relation (1), (2), or (3) are fulfilled for a smaller number of cycles, such as N≤10 in order to reduce asymmetric strain further.

In a most advantageous embodiment, N=1, i.e. balancing in the sense of relation (1), (2), or (3) takes place over each single frame cycle. This greatly simplifies the control of the device because it obviates the need to "plan" the mirror positions over two or more frame cycles.

In the period where the light source is operating and the camera is integrating, the position of each micro-mirror 60 is given by the amount of light to be generated for the respective pixel. Hence, balancing in order to fulfill relation (1), (2), or (3) advantageously takes place during the time when at least one of the following conditions is met:

the camera is not integrating and/or the light source is not lit.

Advantageously, though, the balancing takes place when the light source is not lit, thereby reducing the risk of unwanted flicker in the patient's eye.

Note that t1 and t2 are typically different for at least some of the micro-mirrors, i.e. t1 and t2 are, in a most general case, dependent on the location i, j of the mirror in the modulator, i.e. t1 (i,j) may differ from t1(i',j') if i≠i' and/or j≠j'.

For example, one pixel may be kept dark while integrating the image, and another pixel may be kept bright while integrating the image. It may even be that a third pixel may be kept bright over a first part of the integration and switched to dark for a second part of the integration in order to achieve a pixel-wise brightness-modulation. In these cases, the times t1 and t2 may be different for both or all three types of pixels.

The present technique is particularly important if there is only a single light source or if there are several light sourced that are, however, switched on in an overlapping mater, i.e. if there is at least one time in the frame cycle (in particular during while the camera integrates an image, i.e. records a frame) where all the light sources are switched on. This is in contrast to RGB-projector-systems, where the color channels are projected consecutively, i.e. where only one color channel is active at a time—in such systems, balancing is achieved more easily.

Brightness and/or Color Monitoring

Illumination device 9 may further comprise at least one light sensor for monitoring the brightness of the light source(s).

Such a sensor allows to monitor and control the brightness of the light sources 22*a*-22*d* as their efficiency changes with temperature and depending on the age of the light sources.

In particular, control unit 32 can be adapted to monitor the brightness of the light sources for generating calibration parameters and to use these calibration parameters for controlling the light sources, e.g. by adjusting the currents to the light sources.

For example, and as shown in FIG. 2, there may be one such light sensor 58a, 58b, 58c, 58d attributed to each one light source 22a, 22b, 22c, 22d, which is positioned to receive part of the light from its light source and to generate a signal indicative of its brightness.

Advantageously, however, there may be a single light sensor 58 positioned to measure light from all of several light sources 22a-22d. This can e.g. be achieved by a sensor 58 located at a position where the light from all light sources 22a-22d is combined, e.g. by using the spurious reflection of dichroic beam splitter 42c, which is the last dichroic beam splitter. It is optimized to cast all light towards spatial light modulator 24. However, since it is, in reality, not an ideal dichroic beam splitter, a small fraction of the light from each light source is reflected out of the optical axis of the illumination device and can be used for monitoring the brightness by means of light sensor 58.

In this embodiment, in order to individually measure the brightness of the individual light sources, control unit 32 can be equipped to perform calibration measurements outside the integration phase of camera 16. Such a calibration measurements may comprise the steps of Placing spatial light modulator 24 into a non-transmitting configuration, Switching on exactly one of the light sources 22a-22d and measuring a brightness signal for this light source by means of light sensor 58.

This scheme is, as mentioned, best performed when the device comprises a light sensor 58 positioned to measure light from all of several light sources. In particular, this light sensor is arranged to receive off-axial light from a last dichroic beam splitter used for combining the light of the light sources.

Such calibration phases are carried out for all light sources sequentially, either in the same frame cycle or in separate frame cycles of camera 16.

The calibration phases may e.g. be inserted during, immediately before or immediately after operating phases I2 or I4.

Optionally, the patterns in configurations I2 and I4 may be adapted to compensate for the time the mirrors are spending in their off-position during the calibration phases in order to maintain the condition of Eq. (1).

This kind of monitoring is particularly useful when the illumination device comprises several light sources 22a-22d of different colors, such as red, green, and blue LEDs. In this case, the brightness of each one of them can be monitored, which allows to adjust the relative brightness values of the light sources in order to maintain a desired spectral composition (i.e. color tone, such as a desired color temperature of normally white light), advantageously in a control loop.

Hence, advantageously, the light sources 22a-22d have different colors (i.e. their center wavelength differ by at least 20 nm). In that case, the method performed by the control unit of the device may comprise the step of using the calibration measurements for the light sources 22a-22d in order to maintain a desired relative brightness between at least two of the light sources 22a-22d when said at least two light sources are simultaneously switched on while recording a frame by means of the camera.

NOTES

In the embodiments above, illumination device 9 comprises several individual light sources 22a-22d, e.g. two, three, four or even more light sources. It may, however, also comprise only a single light source, such as a white LED.

In the first aspect of the invention, camera 16 generates the master signal for triggering illumination device 9, i.e. the signal "camera synch" in FIG. 3 is generated by camera 16. In other implementations of the invention, however, camera 16 may also operate in triggered mode, i.e. it integrates a frame upon receiving an external trigger. In that case, control unit 32 may e.g. generate the trigger signal, triggering the recording of a frame by means of camera 16, i.e. the signal "camera synch" in FIG. 4 may not be generated by camera 16 but by control unit 32.

While there are shown and described presently preferred embodiments of the invention, it is to be distinctly understood that the invention is not limited thereto but may be otherwise variously embodied and practiced within the scope of the following claims.

The invention claimed is:

1. An ophthalmologic microscope, comprising:
i) an illumination device generating illumination pulses and having
   a) at least one light source generating light,
   b) an electronically controlled spatial light modulator spatially modulating the light from the light source before it hits a patient's eye and comprising a two-dimensional array of micro-mirrors individually deflectable into a first and a second position, and
   c) illumination imaging optics projecting an image from the spatial light modulator onto the patient's eye,
ii) a microscope device having
   a) microscope optics and
   b) at least one electronic camera, and
iii) a control unit,
   wherein said control unit brings, for a group of $N \leq 100$ consecutive frame cycles of said camera, each micro-mirror of said spatial light modulator into the first position during a time t1 and into the second position during a time t2, wherein $0.1 < t1/t2 < 10$.

2. The microscope of claim 1, wherein at least one of the following conditions applies:

$$0.2 < t1/t2 < 5;$$

$$t1/t2 > 0.6; \text{ and}$$

$$t1/t2 < 0.4.$$

3. The microscope of claim 1, wherein $N \leq 10$.

4. The microscope of claim 1, wherein $N=1$.

5. The microscope of claim 1, wherein said control unit pulses said light source.

6. The microscope of claim 5, wherein the control unit brings the pixels into a given configuration during a dark phase prior to a given light pulse, and starts the light pulse only when the pixels are in the given configuration.

7. The microscope of claim 5, wherein said control unit generates, for each frame recorded by said camera, at least two separate light pulses, wherein one of the light pulses falls into the integration phase of the camera while the other light pulse(s) fall outside the integration phase.

8. The microscope of claim 7, wherein
the light pulses have equal durations,
for all light pulse(s), the spatial light modulator has the same configurations, and
the light pulses are separated by dark phases of equal length.

9. The microscope of claim 8, wherein said control unit brings, between the light pulses, the spatial light modulator into configurations opposite to the configurations during the light pulses.

10. The microscope of claim 1, further comprising at least one light sensor measuring a light intensity between said light source and said spatial light modulator, wherein said control unit brings said light modulator into a non-transmitting mode, and while said light modulator is in said non-transmitting mode, pulses said at least one light source to measure a brightness of said light source.

11. The microscope of claim 1, further comprising at least one light sensor monitoring a brightness of the light source, wherein said control unit monitors the brightness of the light source by said light sensor to generate calibration parameters and uses the calibration parameters to control the at least one light source.

12. The microscope of claim 11, comprising several light sources, wherein said control unit carries out calibration measurements outside an integration phase of said camera, wherein carrying out of said calibration measurements comprises:

placing said spatial light modulator into a non-transmitting configuration, and switching on exactly one of the light sources and measuring a brightness signal by the light sensor.

13. A method for operating an ophthalmologic microscope, wherein said device comprises:

i) an illumination device having a) at least one light source generating light, b) an electronically controlled spatial light modulator comprising a two-dimensional array of micro-mirrors individually deflectable into a first and a second position, and c) illumination imaging optics, ii) a microscope device having a) microscope optics and b) at least one electronic camera, and iii) a control unit, wherein said method comprises spatially modulating the light from the light source with the spatial light modulator before the light hits a patient's eye, projecting an image from the spatial light modulator onto the patient's eye, and bringing, for a group of N≤100 consecutive frame cycles of said camera, each micro-mirror of said spatial light modulator into the first position during a time t1 and into the second position during a time t2, wherein 0.1<t1/t2<10.

14. The method of claim 13, comprising pulsing said light source in a manner synchronized with said frame cycles.

15. The method of claim 14, comprising bringing the pixels into a given configuration during a dark phase prior to a given light pulse, and starting the light pulse only when the pixels are in the given configuration.

16. The method of claim 14, comprising generating, for each frame recorded by said camera, at least two separate light pulses, wherein one of the light pulses falls into the integration phase of the camera while the other light pulse(s) fall outside the integration phase.

17. The method of claim 16, wherein the light pulses have equal durations, for all light pulses, the spatial light modulator has the same configurations, and the light pulses are separated by dark phases of equal length.

18. The method of claim 17, comprising bringing, between the light pulses, the spatial light modulator into configurations opposite to the configurations during the light pulses.

19. The method of claim 13, wherein said device further comprises at least one light sensor measuring a light intensity between said light source and said spatial light modulator, wherein said method comprises bringing said light modulator into a non-transmitting mode, and while said light modulator is in said non-transmitting mode, pulsing said at least one light source for measuring a brightness of said light source.

20. The method of claim 13, wherein said microscope comprises at least one light sensor, monitors a brightness of the light source by said light sensor and generating calibration parameters and uses the calibration parameters to control the light source.

21. The method of claim 20, wherein said microscope comprises several light sources, wherein said method comprises calibration measurements outside an integration phase of said camera, wherein said calibration measurements comprise placing said spatial light modulator into a non-transmitting configuration and switching on exactly one of the light sources and measuring a brightness signal by means of light sensor.

22. The method of claim 13, wherein said microscope comprises a single light source or said microscope comprises several light sources and there is at least one time in the frame cycle where all the light sources are switched on.

23. The method of claim 14, comprising pulsing said light source in a manner synchronized with said frame cycles.

24. The method of claim 21, wherein said light sources have different colors and wherein said method further comprises using the calibration measurements for the light sources in order to maintain a desired relative brightness between at least two of the light sources when said two light sources are simultaneously switched on while recording a frame.

*     *     *     *     *